United States Patent
Vogt

(10) Patent No.: US 10,433,556 B2
(45) Date of Patent: Oct. 8, 2019

(54) TREATMENT AND/OR PROPHYLAXIS OF STORAGE DISEASES OF HARVESTED MATERIAL

(71) Applicant: SOURCON-PADENA GmbH & CO. KG, Tuebingen (DE)

(72) Inventor: Wolfgang Vogt, Tuebingen (DE)

(73) Assignee: SOURCON-PADENA GmbH & CO.KG., Tuebingen (DE)

( * ) Notice: Subject to any disclaimer, the term of this patent is extended or adjusted under 35 U.S.C. 154(b) by 0 days.

(21) Appl. No.: 14/268,548

(22) Filed: May 2, 2014

(65) Prior Publication Data

US 2014/0242052 A1    Aug. 28, 2014

Related U.S. Application Data

(63) Continuation of application No. PCT/EP2012/071278, filed on Oct. 26, 2012.

(30) Foreign Application Priority Data

Nov. 4, 2011 (DE) .................. 10 2011 117 895

(51) Int. Cl.
  *A01N 63/02* (2006.01)
  *A01N 63/00* (2006.01)
  *A01N 43/50* (2006.01)
  *A23B 7/155* (2006.01)

(52) U.S. Cl.
  CPC ............. *A01N 63/02* (2013.01); *A01N 43/50* (2013.01); *A01N 63/00* (2013.01); *A23B 7/155* (2013.01)

(58) Field of Classification Search
  None
  See application file for complete search history.

(56) References Cited

U.S. PATENT DOCUMENTS

| | | | | |
|---|---|---|---|---|
| 6,156,560 | A * | 12/2000 | Chun | A01N 63/00 424/405 |
| 6,916,650 | B2 * | 7/2005 | Arndt | A01N 63/00 435/253.3 |
| 2003/0104511 | A1 * | 6/2003 | Tanzer | C12N 9/0008 435/25 |
| 2007/0123541 | A1 * | 5/2007 | Grosjean-Cournoyer | A01N 43/30 514/254.07 |
| 2011/0257009 | A1 * | 10/2011 | Seitz | A01N 43/90 504/100 |

FOREIGN PATENT DOCUMENTS

| | | |
|---|---|---|
| CA | 2396655 | 6/2001 |
| DE | 698 13 337 | 3/2004 |
| DE | 199 57 378 | 12/2005 |
| DE | 10 2009 051 850 | 12/2010 |
| DE | 10 2009 051 851 | 12/2010 |
| EP | 0 857 421 | 4/2003 |
| WO | 01/03507 | 1/2001 |
| WO | 2011/051104 | 5/2011 |
| WO | 2011/051105 | 5/2011 |
| WO | 01/40441 | 6/2011 |

OTHER PUBLICATIONS

EFSA Journal 2012; 10(12):2954, pp. 1-32.*
Encyclopedia of Life, Solanum tuberosum, retrieved from the internet, Sep. 23, 2015: http://eol.org/pages/482935/overview.*
Tariq et al., Biological Control of Potato Black Scurf by Rhizosphere Associated Bacteria, Brazilian Journal of Microbiology (2010) 41: 439-451.*
Commercial Potato Production in North America , The Potato Association of America Handbook (pp. 1-90), (2010).*
Canadian Examination Report dated Mar. 12, 2015 from Canadian Patent Application No. 2,854,407.
Wikepedia: Imazalil; http://de.wikipedia.org/wiki/Imazalil; printed Jun. 5, 2012.

\* cited by examiner

*Primary Examiner* — Thomas J. Visone
*Assistant Examiner* — Evelyn Y Pyla
(74) *Attorney, Agent, or Firm* — Casimir Jones, S.C.; Tanya Arenson

(57) ABSTRACT

The present invention relates to the treatment and/or prophylaxis of storage diseases of harvested material. This object is achieved by the use of the bacterium of *Pseudomonas* sp. Proradix (DSMZ 13134). This object is further achieved by a method comprising provision of harvested material, contacting said harvested material with a solution containing the bacterium of *Pseudomonas* sp. Proradix (DSMZ 13134), and storing the harvested material outside of the ground soil.

4 Claims, 3 Drawing Sheets

US 10,433,556 B2

TREATMENT AND/OR PROPHYLAXIS OF STORAGE DISEASES OF HARVESTED MATERIAL

CROSS-REFERENCE TO RELATED APPLICATIONS

This application is a continuation of copending international patent application PCT/EP2012/071278 filed on 26 Oct. 2012 and designating the U.S., which has been published in German, and claims priority from German patent application DE 10 2011 117 895.7 filed on 4 Nov. 2011. The entire contents of these prior applications are incorporated herein by reference.

FIELD

The present invention relates to the treatment and/or prophylaxis of storage diseases of harvested material.

BACKGROUND

After the harvest the harvested material is usually stored in large amounts in storage rooms until the further processing or sale. During this storage so-called storage diseases can develop which may damage the harvested material. Storage diseases do not only result in direct deficiencies of the harvested material, but may also cause a permanent deterioration of quality due to a damage of the reproduction cascade of the plant material.

Well-known storage diseases of the potato plant (*Solanum tuberosum*) are tuber blights and scurf diseases. The brown blight, the potato pox, the wet blight and the potato dry blight belong to the tuber blights. The powdery scurf and the silver scurf belong to the scurf diseases.

When it comes to the quality of potatoes, the silver scurf comes more and more to the fore. It becomes noticeable through its silvery grey-brown spots formed on the skin of a potato. The pathogenic agent of the silver scurf is the fungus *Helminthosporium solani*. It is unrelated to the ordinary potato scurf which is induced by a bacterium, or to the powdery scab which is induced by a lower fungus. *Helminthosporium solani* belongs to the class of the ascomycetes, the so-called real sac fungi. *Helminthosporium solani* only affects the potato tuber. It cannot be found at the potato plant above the ground. The disease is limited to the surface of the tuber. At the time of the harvest slightly recessed, brownish spots are visible. In the course of aging the spots become darker and appear silvery. The affection can spread over the entire surface of the tuber. The conidia carriers of the fungus with the dark spores are predominantly located on the brink of the spots and may confer them a fuliginous appearance. The silvery spots result from the pathogenic agent developing in the cork layer of the tuber skin and detaching it from the cortical parenchyma. The destruction of the tuber skin favors the natural loss of water through evaporation since the skin is abrogated as a natural evaporation barrier. The affection by silver scurf therefore results in a weight reduction of potato tubers and a premature dehydration. Another damage is based on the fact that the so-called eyes or germs of the potatoes may be affected and killed resulting in a reduced and incomplete sprouting of affected harvested material. As a result the potato tuber is no longer edible.

The development of storage diseases such as the silver scurf is currently essentially prevented by the heating of the harvested material. Various chemicals are available for this purpose. The most important chemical is the Imazalil which is e.g. distributed under the trade name Magnate®. A drawback is that Imazalil is hazardous to the environment and harmful to the health. Imazalil is toxic for fish and causes damages to birds and ducks. The half-life for the degradation in the ground is about half a year. Imazalil remains in the ground and is not washed out.

SUMMARY

Against this background an object underlying the invention is to provide an alternative subject matter for the treatment and/or prophylaxis of storage diseases of harvested material by means of which the disadvantages of the currently used chemical agents will be avoided.

This object is achieved by the use of the bacterium of *Pseudomonas* sp. Proradix (DSMZ 13134).

This object is further achieved by a method comprising the following steps:
a) provision of harvested material,
b) contacting said harvested material with a solution containing the bacterium of *Pseudomonas* sp. Proradix (DSMZ 13134), and
c) storing the harvested material outside of the ground soil.

The *Pseudomonas* strain of Proradix which was deposited on 3 Nov. 1999 under the deposition number DSM 13134 at the DSMZ, 38124 Braunschweig, Germany, according to the Budapest Treaty, is a species within the RNA group I of the Pseudomonadaceae. A final classification of Proradix has not been made so far, even though there are hints indicating a relationship to *Pseudomonas fluorescens*.

The effectiveness of the *Pseudomonas* strain of Proradix for the prophylaxis and treatment of storage diseases of harvested material was surprising and could not be expected.

The deposited *Pseudomonas* strain of Proradix is extensively described in WO 01/40441 to which reference is made herewith. There it is described an effect of Proradix against the black blight of salad and brown blight of potato tubers. Both plant diseases are caused by the basidiomycete of *Rhizoctonia solani*.

In the WO 2011/051104 the effect of Proradix against an affection of the potato tuber or cucumber by the "Oomycetes" or Peronosporomycetes of *Phytophthora* and *Pythium* is described.

In the WO 2011/051105 the effect of Proradix against an affection of the potato tuber by the bacterium *Erwinia* sp. is described.

In the literature it is further mentioned that the *Pseudomonas* strain of Proradix gives protection against an affection of plants or seed material by the fungus of the genus of *Fusarium* sp.

In all cases described in the art the *Pseudomonas* strain of Proradix shows its protective effects exclusively in the ground soil. For this purpose the harvested material such as the tubers of a seed potato is incubated with the *Pseudomonas* strain of Proradix before placing them into the ground soil. It is therefore assumed in the art that Proradix requires the ground soil as the natural environment of its habitat to exert the described protective effects on the plants and its fruits.

For this reason it was surprising and could not be expected that Proradix also shows protective effects against storage diseases such as the silver scurf outside of the ground soil, namely e.g. in the potato storage. In the storage rooms climatic conditions prevail which are completely different from those in the ground soil. For example, lower temperatures of about 4° Celsius may prevail over a longer time period. In addition, nutrient matter and the humid environment as provided by the ground soil and the root are widely absent. Under conditions of such kind neither high physiological activities of the *Pseudomonas* strain of Proradix nor the induction of defense mechanisms in the harvested material can be expected. Nevertheless, the inventors were able to find out that after a treatment of the potato tuber with Proradix outsight of the ground soil before the storing results in a reduction of the silver scurf of about 50% in comparison to untreated potato tubers.

In contrast to chemicals which are so far employed for the treatment of storage diseases the use of Proradix does not result in any toxic residues. For this reason the invention is also applicable in ecologically operating establishments.

According to the invention "harvested material" refers to agricultural fruits and plants which were removed from their natural environment for the purpose of a later consumption or further processing. Important harvested materials according to the invention are tuber fruits such as the potato tuber.

According to the invention "storing" or "storage" refers to the introduction of the harvested material into storage facilities, i.e. outside of the ground soil. Such storage facilities are generally dark rooms or halls comprising temperatures of 4° C. to 10° C. and an air humidity of about 90% over the entire year to prevent a germination or a "freezing" of the harvested material.

An object underlying the invention is herewith completely achieved.

In another embodiment the storage disease is caused by the fungus of *Helminthosporium solani* (silver scurf).

This measure has the advantage that the invention combats in a targeted manner one of the most important storage diseases.

In another embodiment of the method according to the invention before step a) the following steps are performed:
a') provision of plants and/or seed material,
a") contacting said plants and/or seed material with a solution containing the bacterium of *Pseudomonas* sp. Proradix (DSMZ 13134),
a''') introducing said plants/seed material into the ground soil,
a'''') cultivating said plants/seed material in the ground soil, and
a''''') yielding of the harvested material.

This measure has the advantage that a synergistic effect of the *Pseudomonas* strain of Proradix on the harvested material is generated which has been realized by the inventors for the first time. In this embodiment a treatment of the material at two times with the Proradix is carried out, namely first at the laying, i.e. the introduction of the plants or the seed material into the ground soil, and a second time, namely before the storing of the harvested material in a storage facility. As the inventors were able to realize, by such a treatment at two times the affection by silver scurf is dramatically reduced. The observed effect of the treatment at two times is synergistic i.e. larger than the sum of the respective effects of a single treatment of the material either only at the laying or only before the storage.

In another embodiment of the method according to the invention it is preferred if in step b) and step a"), if applicable, the solution is administered through mordanting, spraying or immersing of the harvested material and, if applicable, the plants or seed material, respectively.

As the inventors were able to realize, a uniform moistening of the surface of the harvested material or the plants or seeds, respectively, is one of the crucial factors for an optimum effect. This uniform moistening can be realized by means of the before mentioned measures.

In another embodiment of the use according to the invention and the method according the invention the harvested material and, if applicable, the seed material are tubers of the potato plant (*Solanum tuberosum*).

This measure has the advantage that one of the most important economic plants with a huge economic significance, which is very often affected by storage diseases such as the silver scurf, can be effectively protected or treated, respectively. As the inventors were able to demonstrate Proradix brings particularly good results in this specific case.

In another embodiment of the use according to the invention, the bacterium of *Pseudomonas* sp. Proradix is used in combination with a chemical that is effective against storage diseases, such as Imazalil.

According to this, in another embodiment of the method of the invention instead of step a") the following step is performed:
(a*) Contacting the plants and/or the seed material with a chemical that is effective against a storage disease, such as Imazalil.

As the inventors have realized, the effectiveness of the *Pseudomonas* strain of Proradix is not compromised by the combination with chemicals which are so far used in the art, such as e.g. Imazalil. This was surprising since it has been assumed that the chemical damages the bacterium of Proradix in such a way that any protective activity gets lost. However, as the inventors were able to realize, the protective activity of Proradix will be preserved after the use of the chemicals. To the contrary, it could be observed that the activity of the chemical is even intensified by the *Pseudomonas* strain of Proradix, especially when the chemical is used at the laying of the seed material and Proradix is used before the storing of the harvested material.

As a consequence, the *Pseudomonas* strain of Proradix can be used as the sole active agent against the storage disease in the context of a monotherapy, however also in combination with other active agents. By doing so synergistic effects may result.

The *Pseudomonas* strain of Proradix according to the invention can be provided in any formulation, such as e.g. a solution in form of a "storage mordant" or as a powder. Such formulations are well-known to the skilled person. Examples of formulations are disclosed in WO 01/40441, to which it is explicitly referred. Also such formulations are appropriate which are provided and distributed by the company of Sourcon Padena GmbH & Co. KG, Tübingen, Germany.

The invention further relates to a method for producing a composition for the treatment and/or prophylaxis of storage diseases of harvested material, comprising the following steps:
(a) provision of the bacterium of *Pseudomonas* sp. Proradix (DSMZ 13134) in an amount which is therapeutically active in/for plants and
(b) formulating of the bacterium.

The features, advantages, and characteristics of the use according to the invention apply correspondingly to the method for producing according to the invention.

It should be understood that the before mentioned features and those to be explained in the following can not only be used in the specifically indicated combination, but also in other combinations or in isolated manner without departing from the frame of the present invention. The invention is now further explained by means of examples from which further features, characteristics and advantages will result. The examples are for the purpose of illustration and do not restrict the scope of the invention.

EXAMPLES

Example 1

Isolation of Proradix

The isolation of the bacterium of *Pseudomonas* sp. Proradix is extensively described in WO01/40441, there example 1. It is explicitly referred thereto and such disclosure is made a disclosure of the present application. The bacterium is also purchasable from the company of Sourcon Padena GmbH & Co. KG, Tübingen, Germany.

Example 2

Dosage and Application

For the treatment of the seed potato at or before the laying into the ground soil Proradix is used as a liquid mordant [Proradix WG (LF 4816-00); Sourcon Padena GmbH & Co. KG, Tübingen, Germany], according to the information of the manufacturer in a concentration of 60 g/ha via the spraying method by using a ULV spraying device. Before the storage of the potatoes 20 g of Proradix WG is dissolved in a maximum of 2 l of water per barrel. The application onto the potatoes is also effected by means of a ULV spraying device.

Example 3

Field Trials

The laying of the potato and, if applicable, the treatment with Proradix and/or Imazalil is carried out in springtime and the harvest and storage and, if applicable, the treatment with Proradix and/or Imazalil is carried out in fall of the same year.

In a field trial conducted in the years of 2010/2011 in Germany according to the EPPO guidelines the effect of Proradix was examined on an affection by the silver scurf of the potato tuber after storing in the storage facility. For this purpose, a part of the potato tubers was remained entirely untreated, another part was only treated at the laying, and yet another part only before the storage, and a further part both at the laying and also before the storage. After a storage time of 20 weeks the potatoes were examined for an affection by the silver scurf. The result is shown in FIG. 1.

Figure 1:
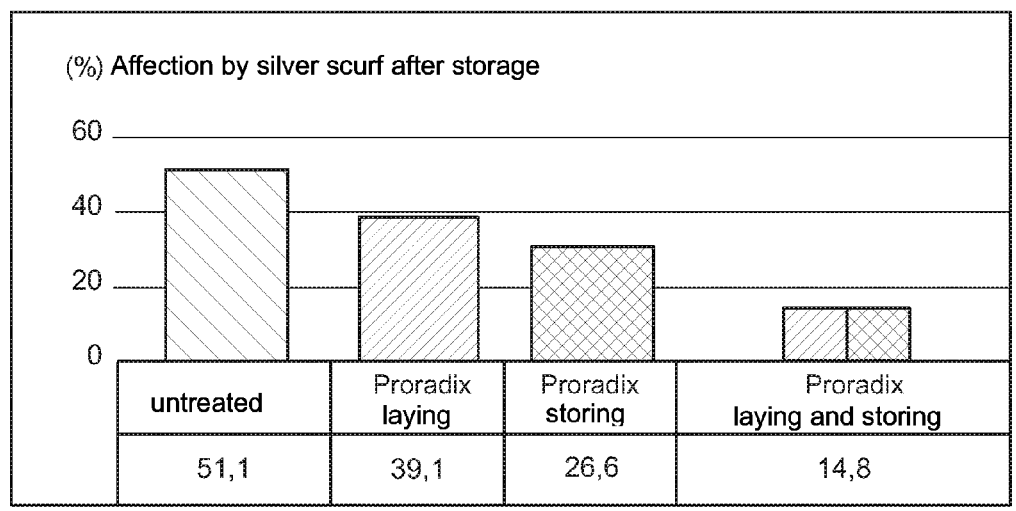
FIG. 1 shows the effect of Proradix on the affection of potato tubers by silver scurf after the storage following a treatment of the potato tuber at the laying and/or before the storage (field trial 2010/2011 in Germany)

It is shown that more than 50% of the surface of the untreated potatoes is affected by silver scurf after the storage (FIG. 1, first column). Following a treatment of the potatoes with Proradix exclusively at the laying an affection by silver scurf after the storage can be seen, which is reduced by about 25% (absolute: 39.1%; FIG. 1, second column). Following a treatment of the potatoes with Proradix exclusively before the storage a reduction of the affection by silver scurf of almost 50% can already be seen (absolute: 26.6%; FIG. 1, third column). After a treatment of the potatoes with Proradix both at the laying and also before the storage in comparison to the untreated potatoes a dramatic reduction of the affection by silver scurf after the storage of more than 70% can be seen (absolute: 14.8%, FIG. 1; fourth column) which implies a synergistic effect (FIG. 1; cf. fourth with second and third column).

In a further field trial conducted in the years of 2010/2011 in the Netherlands according to the EPPO guidelines the influence of Proradix in comparison to the chemical standard of Imazalil on the production of spores of the fungal pathogen of *Helminthosporium solani*, the initiator of the silver scurf, and the rate of germination of the spores on the potato tuber was examined. The results are shown in FIGS. 2 and 3.

Figure 2:
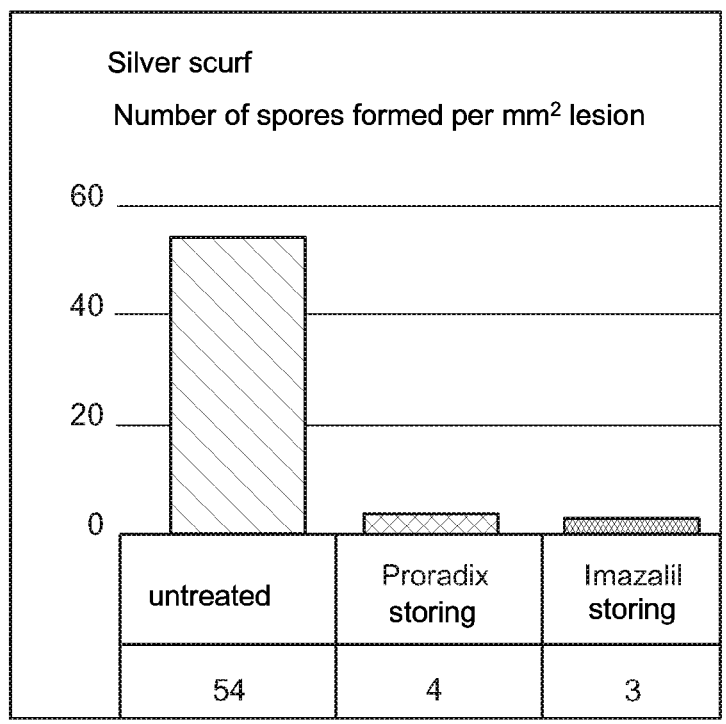
FIG. 2 shows the effect of Proradix in comparison to the chemical of Imazalil on the regeneration of spores of the silver scurf pathogen on the potato tuber after the storage following a treatment of the potato tuber at the laying and/or before the storage (field trial 2010/2011 in the Netherlands)

It is clearly shown that by the treatment of the potato with Proradix before the storage a dramatic reduction of the formation of spores is achieved (FIG. 2; second column) which is comparable to that being achieved by the chemical of Imazalil (FIG. 2; third column).

Figure 3:
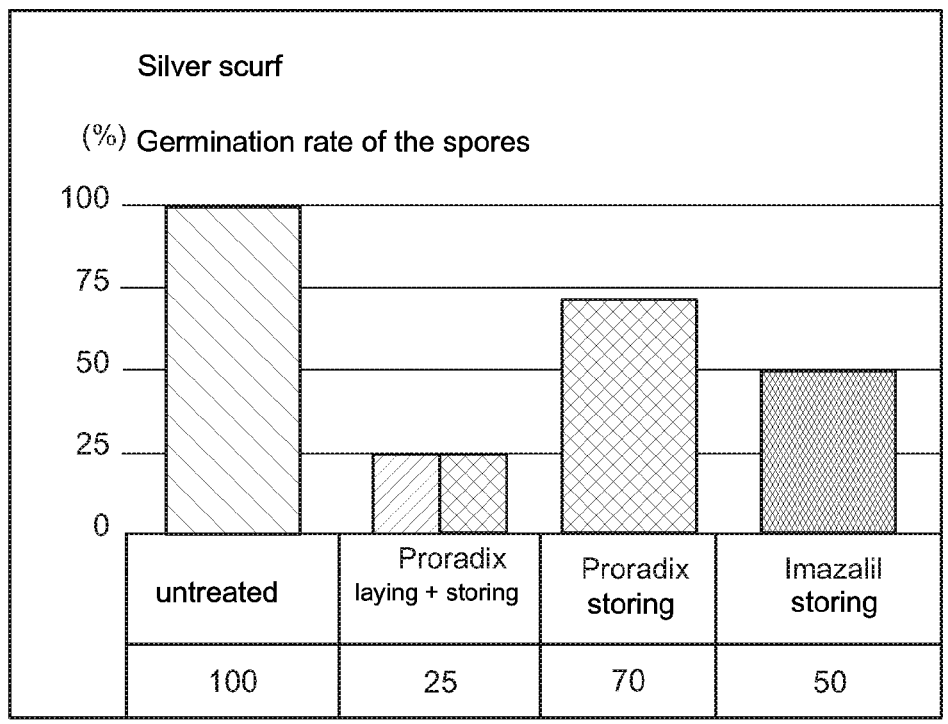
FIG. 3 shows the effect of Proradix in comparison to the chemical of Imazalil on the rate of germination of the spores of the silver scurf pathogen on the potato tuber after the storage following a treatment of the potato tuber at the laying and/or before the storage (field trial 2010/2011 in the Netherlands)

The examination of the formation of spores shows that expecially the combined application of Proradix at the laying but also before the storage of the potatoes, in comparison to untreated potatoes, only a quarter of the formed spores is able to germinate (FIG. 3; second column). Here Proradix shows significant advantages over the chemical of Imazalil, the use of which still enables half of the spores to germinate (FIG. 3; fourth column).

Figure 4:
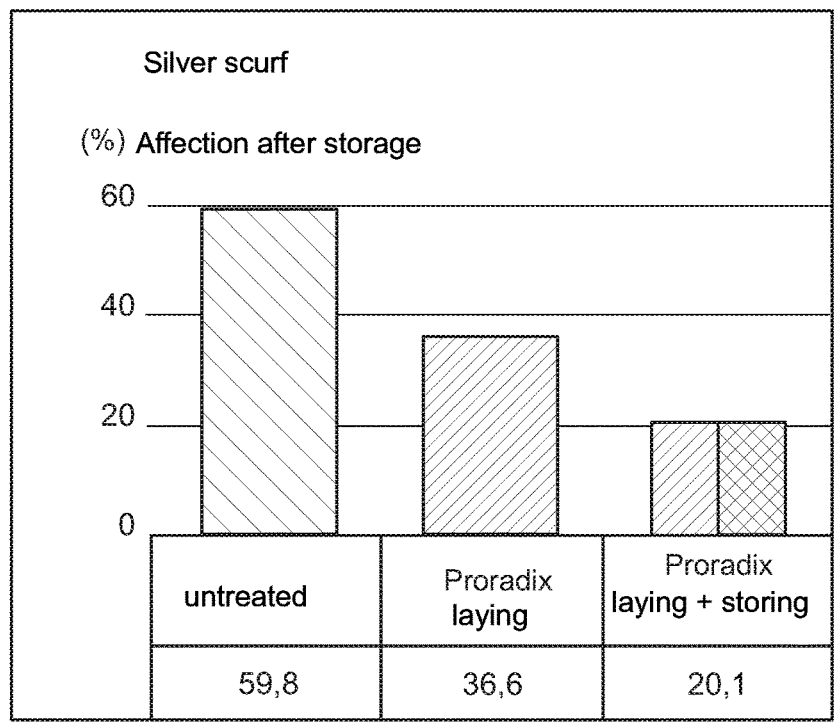
FIG. 4 shows the effect of Proradix on the affection by the silver scurf on potato tubers after the storage following a treatment of the potato tuber at the laying and before the storage (field trial 2009/2010 in the Netherlands)

In another field trial which was conducted in the years of 2009 and 2010 in Germany according to the EPPO guidelines the results shown in FIG. 1 were confirmed. The result of this field trial is shown in FIG. 4.

In a field trial conducted in the years of 2010 and 2011 in Germany according to the EPPO guidelines it was examined in detail, whether Proradix can also be effectively used in combination with the chemical of Imazalil. For this purpose a part of the potatoes remain untreated, a part was treated with the chemical of Imazalil at the laying, and a part was treated at the laying and also before the storage with the chemical of Imazalil, and yet another part was treated at the laying with Imazalil and before the storage with Proradix. The result is shown in FIG. 5.

Figure 5:
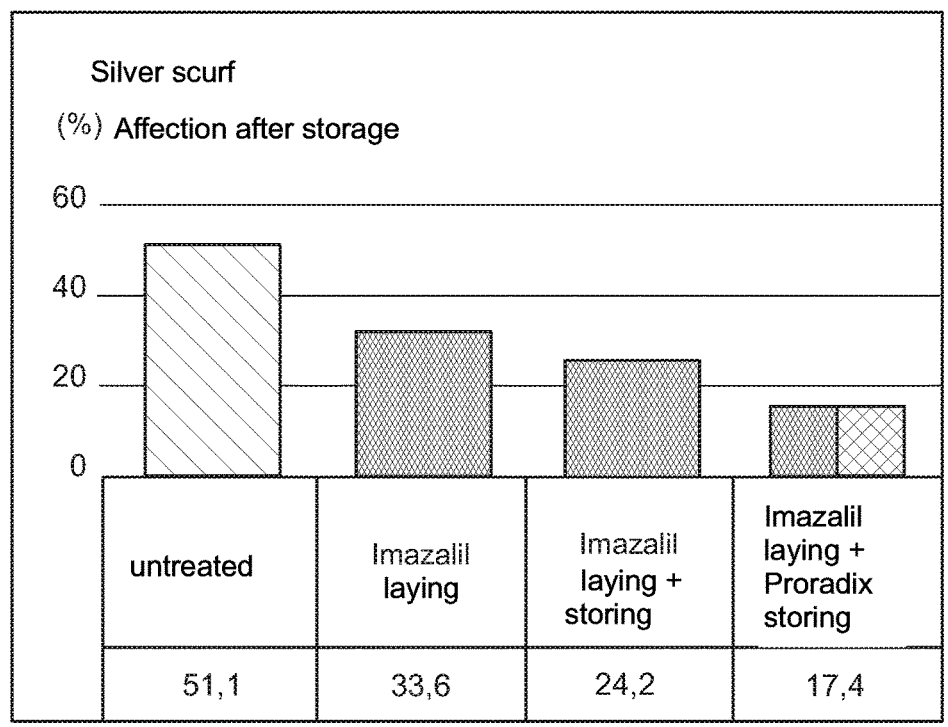
FIG. 5 shows the effect of Proradix in combination with the chemical of Imazalil on the affection by the silver scurf of potato tubers after the storage following a treatment of the potato tuber at the laying and/or before the storage.

It becomes apparent that, in comparison to untreated potatoes, the application of Imazalil at the laying in combination with the application of Proradix before the storage results in a dramatic reduction of an affection by silver scurf after the storage (FIG. 5; cf. fourth with first column), whereas a treatment of the potatoes exclusively with Imazalil at the laying and the storage results in a significantly diminished reduction of the affection by silver scurf after the storage (FIG. 5; cf. third with first column).

CONCLUSION

The inventors were able to demonstrate, using the example of the potato and the silver scurf, that the *Pseudomonas* strain of Proradix can be employed for the treatment and/or prophylaxis of storage diseases of harvested material. The protective effects of the *Pseudomonas* strain of Proradix were so far only described in cases where the bacterium was introduced into the ground soil and given to the root and, therefore, into its natural habitat. As a consequence, the *Pseudomonas* strain of Proradix used as a biological storage mordant is a particular environment-friendly alternative to the chemicals which are so far used.

What is claimed is:

1. A method for reducing growth of *Helminthosporium solani* (silver scurf) on harvested tubers of a potato plant (*Solanum tuberosum*), comprising the following steps:
   a) providing harvested tubers of a potato plant (*Solanum tuberosum*), wherein said harvested tubers are infected with *Helminthosporium solani* (silver scurf),
   b) contacting said harvested tubers with a solution containing *Pseudomonas proradix* strain DSMZ 13134 as the sole active agent, and
   c) storing said harvested tubers outside of a ground soil under atmospheric pressure in a storage room for the purpose of later consumption.

2. The method of claim 1, comprising before step a) the following steps:
   a') providing tubers of the potato plant (*Solanum tuberosum*),
   a") contacting said tubers with a solution containing *Pseudomonas proradix* strain DSMZ 13134,
   a'") introducing said tubers into the ground soil,
   a"") cultivating said tubers in the ground soil, and
   a""') harvesting the cultivated tubers to produce a harvested material, wherein said harvested material is said harvested tubers.

3. The method of claim 1, wherein in step b) the solution is applied by mordanting, spraying or immersing the harvested tubers.

4. The method of claim 2, wherein in step a") and step b) the solution is applied by mordanting, spraying or immersing the tubers.

* * * * *